United States Patent [19]

Mikhail

[11] Patent Number: 5,282,867
[45] Date of Patent: Feb. 1, 1994

[54] PROSTHETIC KNEE JOINT

[76] Inventor: W. E. Michael Mikhail, 4203 Shamley Green, Toledo, Ohio 43623

[21] Appl. No.: 890,961

[22] Filed: May 29, 1992

[51] Int. Cl.$^5$ ............................................. A61F 2/38
[52] U.S. Cl. .................................... 623/20; 623/18
[58] Field of Search ..................... 623/16, 18, 19, 20

[56] References Cited

U.S. PATENT DOCUMENTS

| 3,765,033 | 10/1973 | Goldberg | 623/20 |
| 3,945,053 | 3/1976 | Hillberry et al. | 623/20 |
| 3,969,773 | 7/1976 | Menschik | 623/20 |
| 4,770,663 | 9/1988 | Hanslik et al. | 623/20 |

FOREIGN PATENT DOCUMENTS

| 0178445 | 4/1986 | European Pat. Off. | 623/20 |
| 0303195 | 2/1989 | European Pat. Off. | 623/20 |
| 2122390 | 1/1973 | Fed. Rep. of Germany | 623/20 |
| 2906458 | 8/1979 | Fed. Rep. of Germany | 623/20 |
| 2634373 | 1/1990 | France | 623/20 |
| 2039220 | 8/1980 | United Kingdom | 623/20 |
| 2237200 | 5/1991 | United Kingdom | 623/20 |

*Primary Examiner*—David Isabella
*Attorney, Agent, or Firm*—Emch, Schaffer, Schaub & Porcello Co.

[57] ABSTRACT

A prosthetic knee joint including femoral and tibial component joined together with support means permitting flexing of the knee and rotational movement of the tibia during flexing approaching that of the matural knee. The support means include flexible synthetic ligaments and various configurations of hinge means.

28 Claims, 12 Drawing Sheets

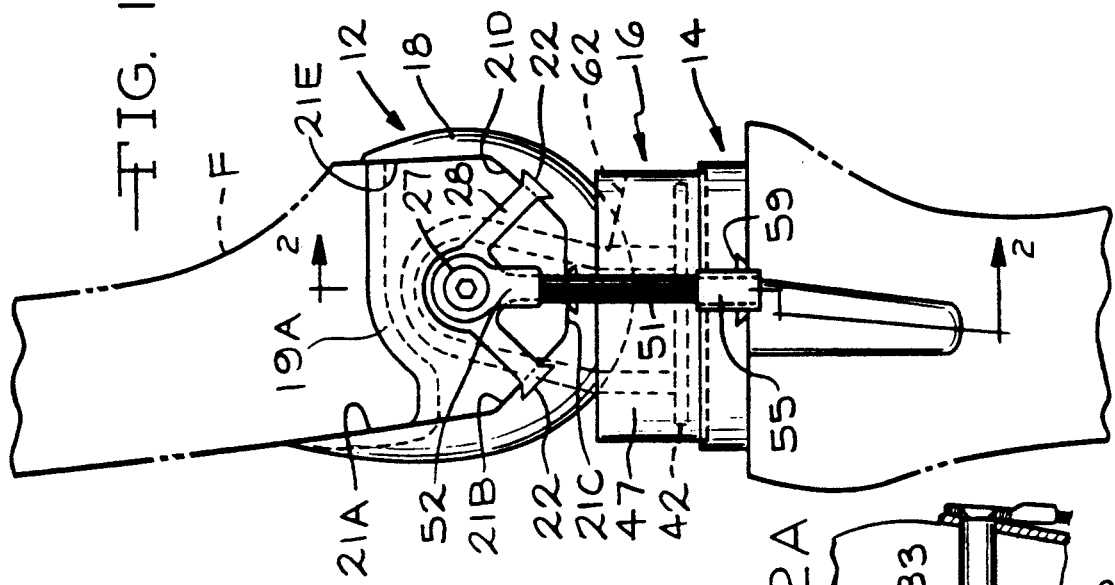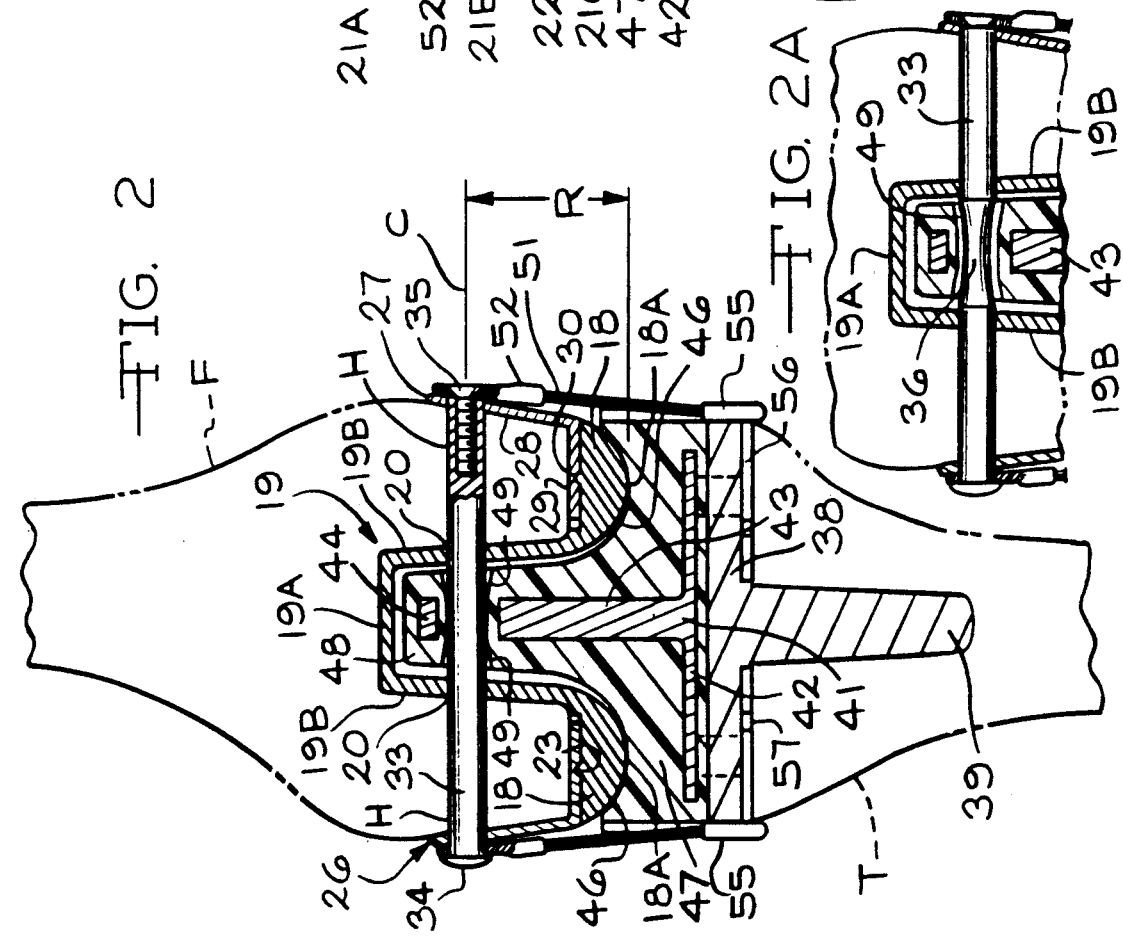

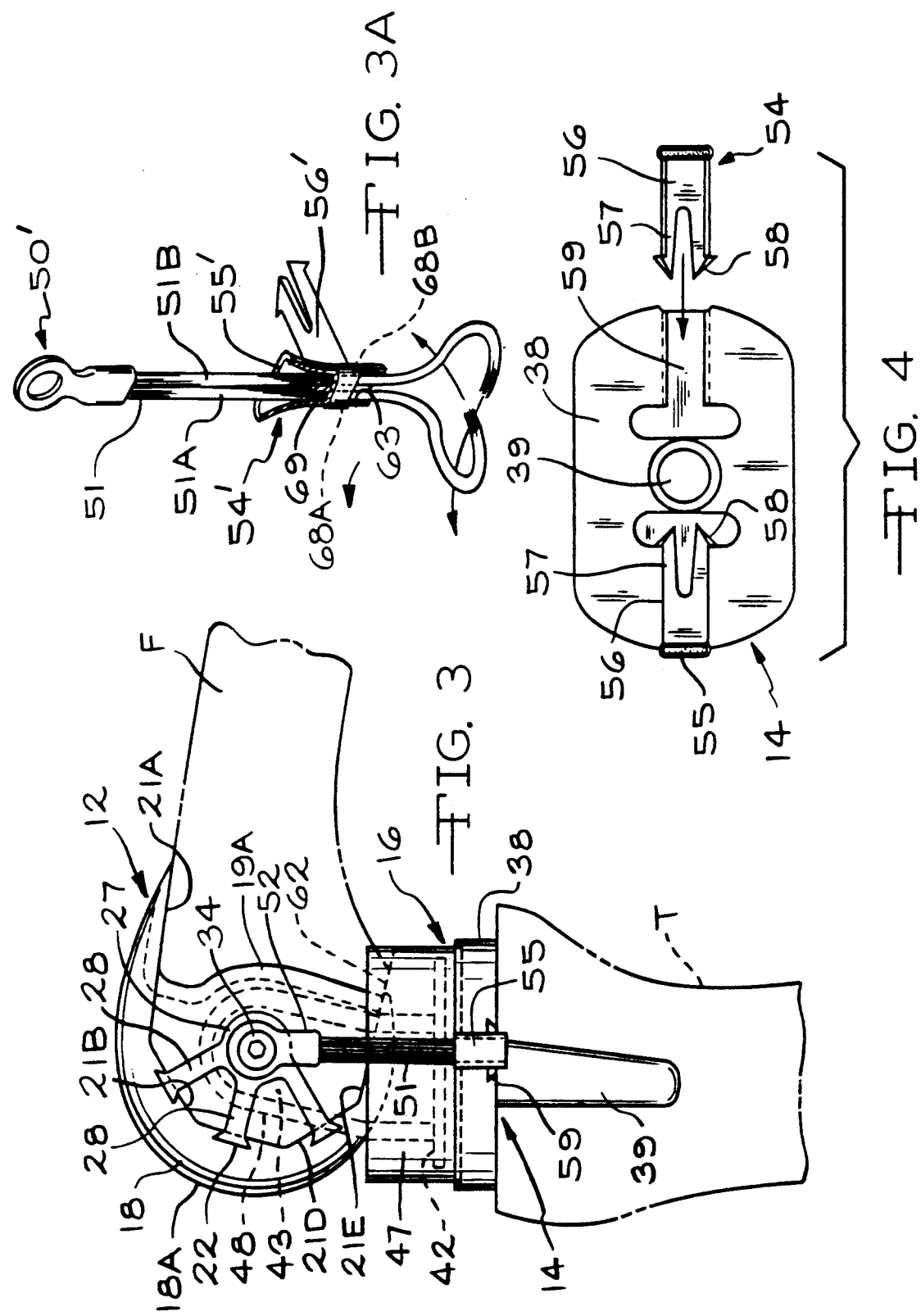

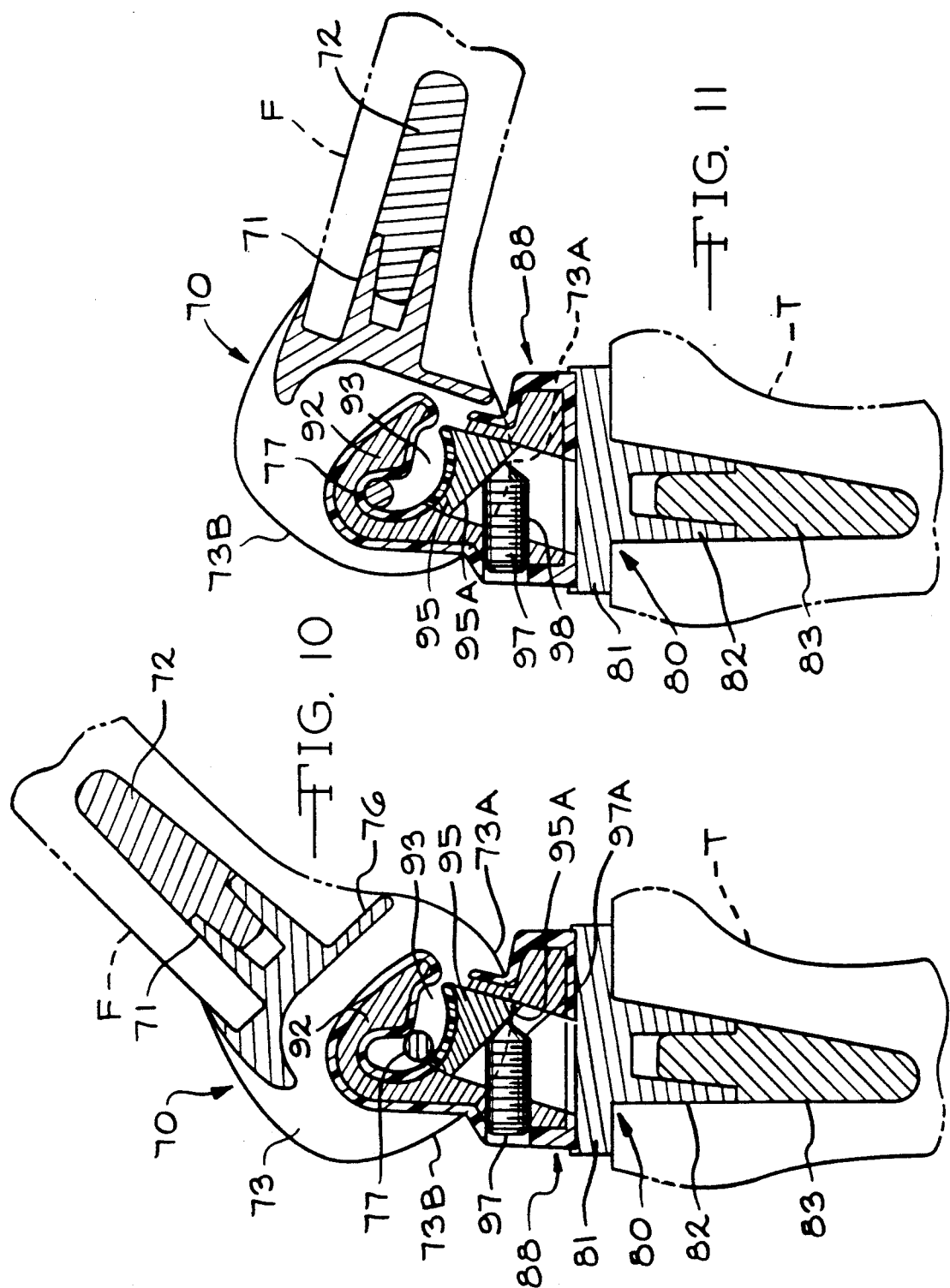

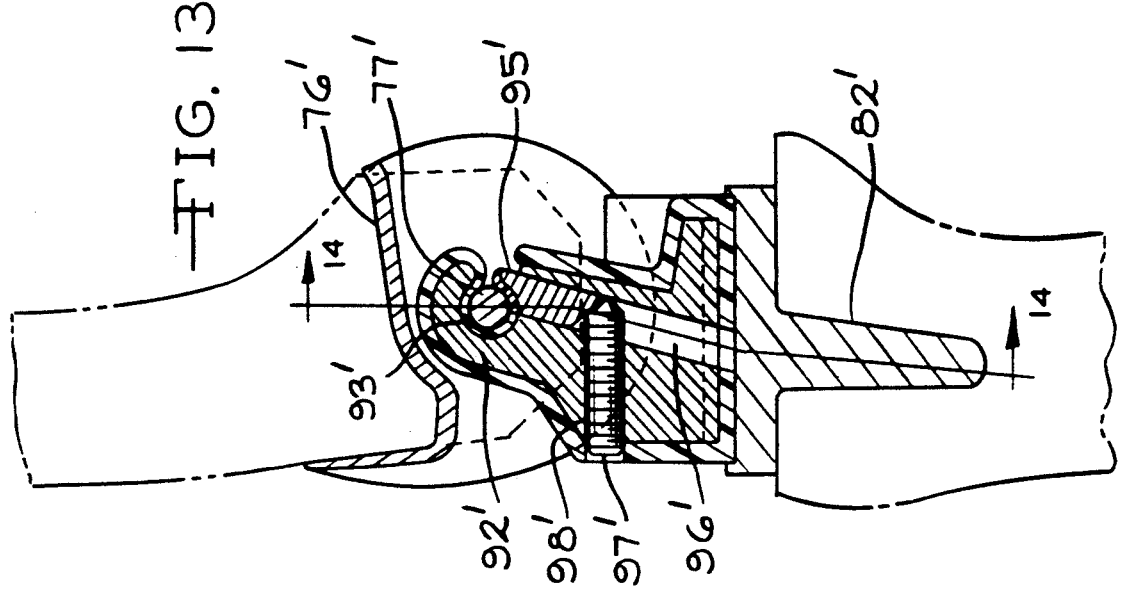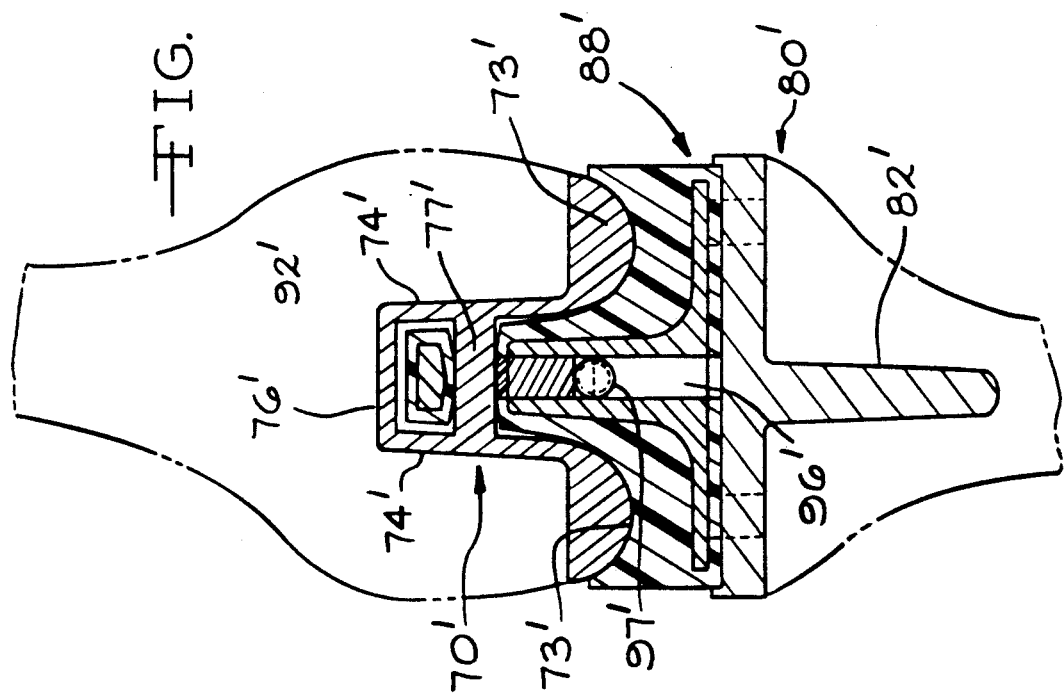

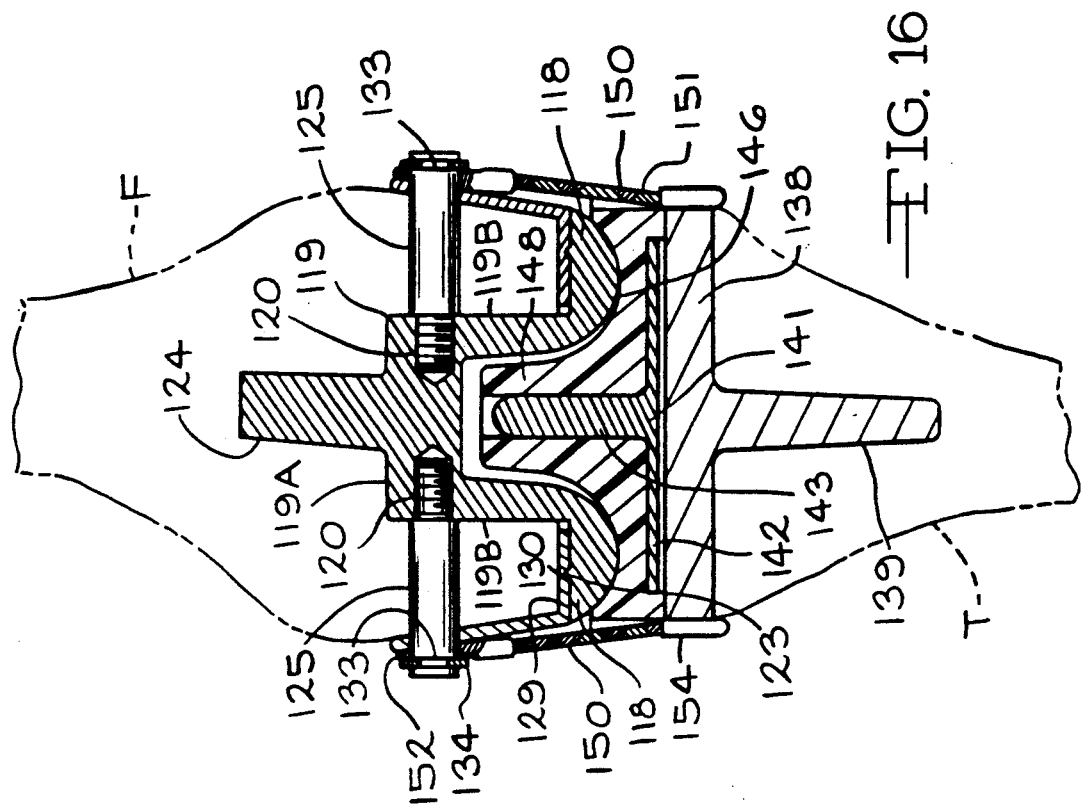
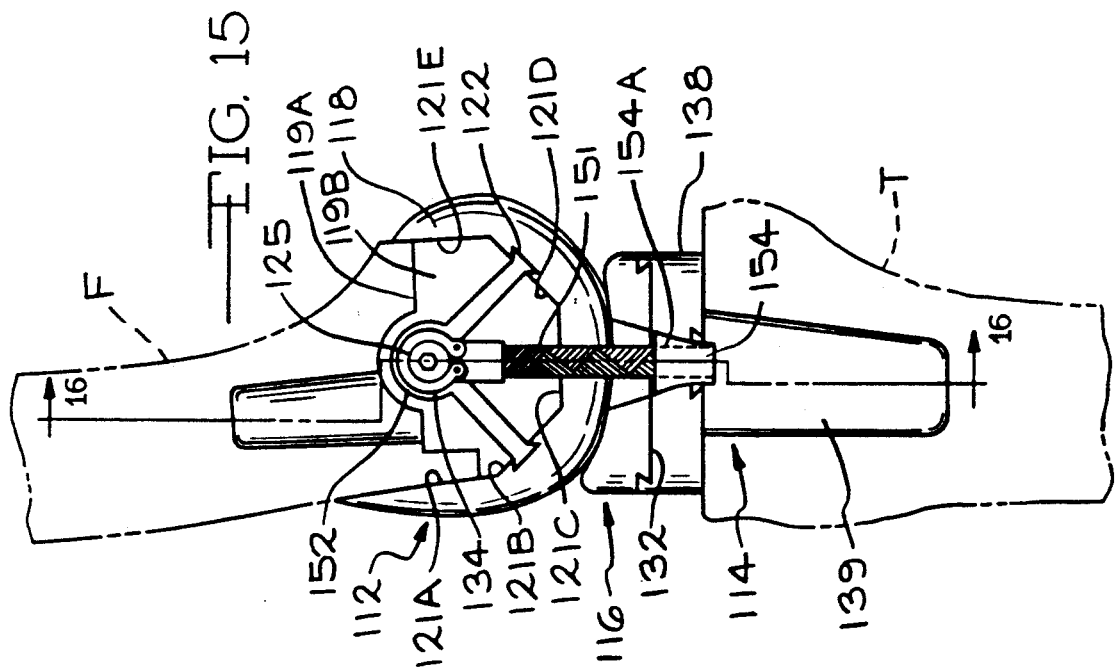

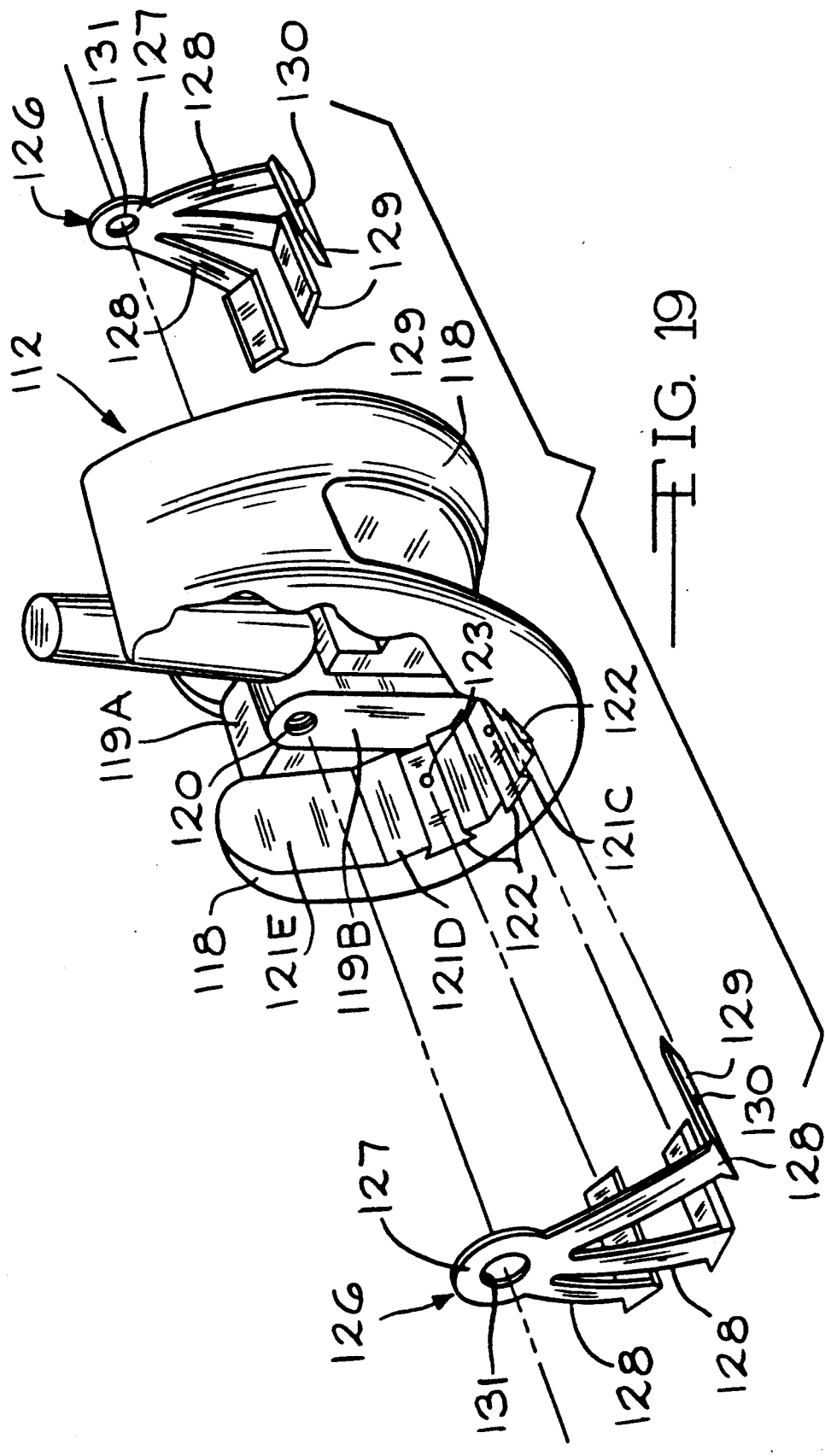

PROSTHETIC KNEE JOINT

BACKGROUND ART

The present invention relates to a prosthetic knee joint and is specifically directed to one which permits functional motion including some rotational movement as the knee moves from flexion to extension and vice-versa. It is particularly well-suited where deterioration of the tissues of the knee joint require augmentation or substitution of the medial and/or lateral collateral ligaments and in cases where there is global instability, bony and ligaments deficiencies or dysfunction.

The development of knee prostheses involves a multitude of factors which must be taken into consideration due to the complexity of the knee. A balancing of such factors is required in order to design a knee prosthesis which provides the necessary support and range of motion over an extended number of years with while maintaining optimal function. It is desirable to remove as little bone as possible and to preserve as much of the soft tissue as possible; however, deterioration from disease or other causes can require extensive removal of bone and augmentation or substitution of the deficient ligaments and other soft tissue.

There is shown in the prior art a variety of types of knee joint prostheses designed to accommodate various specific problems and various amounts of bone removal depending upon the condition of the patient. For example, U.S. Pat. No. 4,301,553, incorporated herein by reference, is directed to a hinged knee joint which is intended to perform in an almost natural anatomical manner utilizing a hinged coupling which is pivotally attached to a flanged stem element having a rod depending thereon and permitting the joint to undergo relative rotation in at least two planes while distributing load forces over substantial bearing areas.

U.S. Pat. No. 3,996,624 discloses another type of prosthetic knee joint having a shaft rotatably mounted in the openings in the condyloid elements of the femoral prosthesis and extending through a hole in the center portion of the tibial prosthesis and is designed utilizing configurations and materials for the respective components to insure that normal wear associated with the bearing surfaces does not change the relative centers of the rotating surfaces and thereby does not introduce excentricity in the concentric bearing system.

U.S. Pat. No. 4,634,444 discloses a knee joint having bearing surfaces of large areas, while U.S. Pat. No. 5,011,496 discloses a prosthetic joint which provides a large area of contact between the bearing surfaces as the knee is flexed while permitting posterior movement of the femoral component relative to the tibial component during flexing. One embodiment of such patent also discloses a constrained or hinged prosthesis.

U.S. Pat. No. 4,714,475 discloses a tibial member of a knee joint endoprosthesis in which an artificial tendon of appropriate plastic material is utilized to secure a patella to a tibial endoprosthesis by fastening ends of the natural tendons of the patella which were severed as part of a resectioning process to such tibial endoprosthesis.

U.S. Pat. No. 3,745,590 relates to an articulating prosthesis which uses a synthetic flexible ligamentous attachment to fasten a shaped thumb joint prosthesis to an adjacent tendon, ligament or bone.

U.K. Patent Specification 1,603,833 discloses a prosthetic knee joint device having elongate flexible members connected under tension between first and second components connected to the upper and lower limb portions of an artificial leg.

Zimmer, Inc. 1981 catalog shows an OFFSET HINGE TM total knee designed for use whenever instability of the knee joint exists due to the absence of cruciate and/or collateral ligaments.

Catalog entitled "The Howmedica ® Kinematic TM Knee System" discloses four knee prosthesis systems including one entitled "The Kinematic Rotating Hinge" having an anatomically similar rotational axis hinge permitting rotational laxity about the tibial axis to reduce stresses at the bone-cement interfaces.

DISCLOSURE OF INVENTION

The present invention is directed to a prosthetic knee joint which under various embodiments utilizes a hinged concept coupled with the concept of utilizing large bearing surfaces. It also provides for the utilization of artificial ligaments for either or both of the medial or lateral collateral ligaments in those instances in which the natural collateral ligaments must be removed or are in deteriorated condition.

BRIEF DESCRIPTION OF THE DRAWINGS

FIG. 1 is a side elevational view of the prosthesis of the present invention showing in dashed lines the femur and tibia to which, respectively, the femoral and tibial components are attached, with the knee, in a position of extension.

FIG. 2 is a sectional view taken through line 2—2 of FIG. 1.

FIG. 2A is a fragmentary sectional view similar to FIG. 2 showing a modified embodiment.

FIG. 3 is a view similar to FIG. 1 showing the position of the respective components with the knee in a position of full flexion.

FIG. 3A is a perspective view, partly in section of one type of connector for fastening synthetic collateral ligaments to the femoral and tibial components.

FIG. 4 is a plan view of the tibial component looking at those portions intended to be implanted in and contact the tibia and showing the connector is fastened to the tibial component.

FIG. 10 is a view similar to FIG. 7 showing the relative positioning of the respective components when the knee is in partial flexion of approximately 30°–45°.

FIG. 11 is a view similar to FIG. 10 showing the relative positioning of the components when the knee is at maximum flexion.

FIG. 13 is a side elevational view, in section, showing yet another embodiment of the present invention.

FIG. 14 is a sectional view taken through line 14—14 of FIG. 13.

FIG. 15 is a side elevational view showing yet another embodiment of the present invention.

FIG. 16 is a sectional view taken through line 16—16 of FIG. 15.

FIG. 19 is an exploded view of the femoral component of the embodiment of FIGS. 15-18.

BEST MODE OF CARRYING OUT INVENTION

Figure 5:
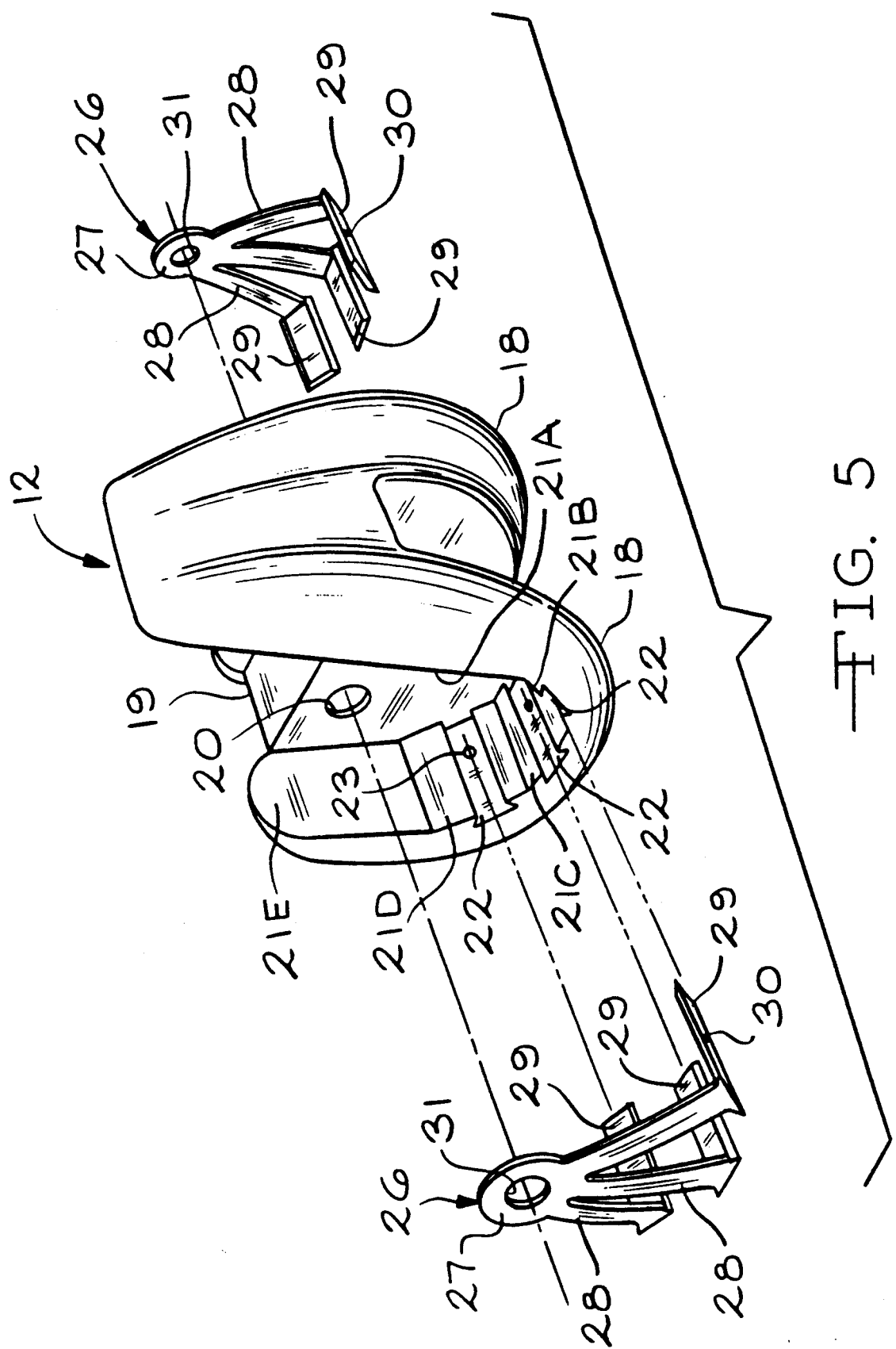
FIG. 5 is an exploded perspective view of the femoral component of the present invention.

Referring now to FIGS. 1-6, there is shown a total knee prosthesis having a femoral component 12 and a tibial component 14 between which is positioned an intermediate tray or plateau 16.

The femoral component 12 is intended to be secured to the prepared distal end of a femur F and includes a pair of identical spaced apart condylar portions 18, each of which has an outer surface smoothly convexly curved in lateral profile similar to the curvature of an anatomical femoral condyle and convexly curved along the antero-posterior extent and following a circular path. Thus, if the lowermost portion 18A of each of the condylar portions 18 as viewed in FIG. 2 is considered to be the apex for any lateral cross section, the path followed along the antero-posterior extent at each such apex will be an arc of a circle having a center lying on the line C and having a radius R.

Integral with and positioned between the condylar portions 18 is a central housing 19 having a top wall 19A and side walls 19B extending between the top wall 19A and the condylar portions 18. Each of the housing side walls 19B has an aperture 20, the centers of which lie on the line C.

The interior of the condylar portions 18 includes a plurality of planar faces 21A, 21B, 21C, 21D and 21E. Three of the planar surfaces, namely, 21B, 21C and 21D have dovetail slots 22 formed therein. Each of the dovetail slots 22 has a raised nub 23.

Figure 6:
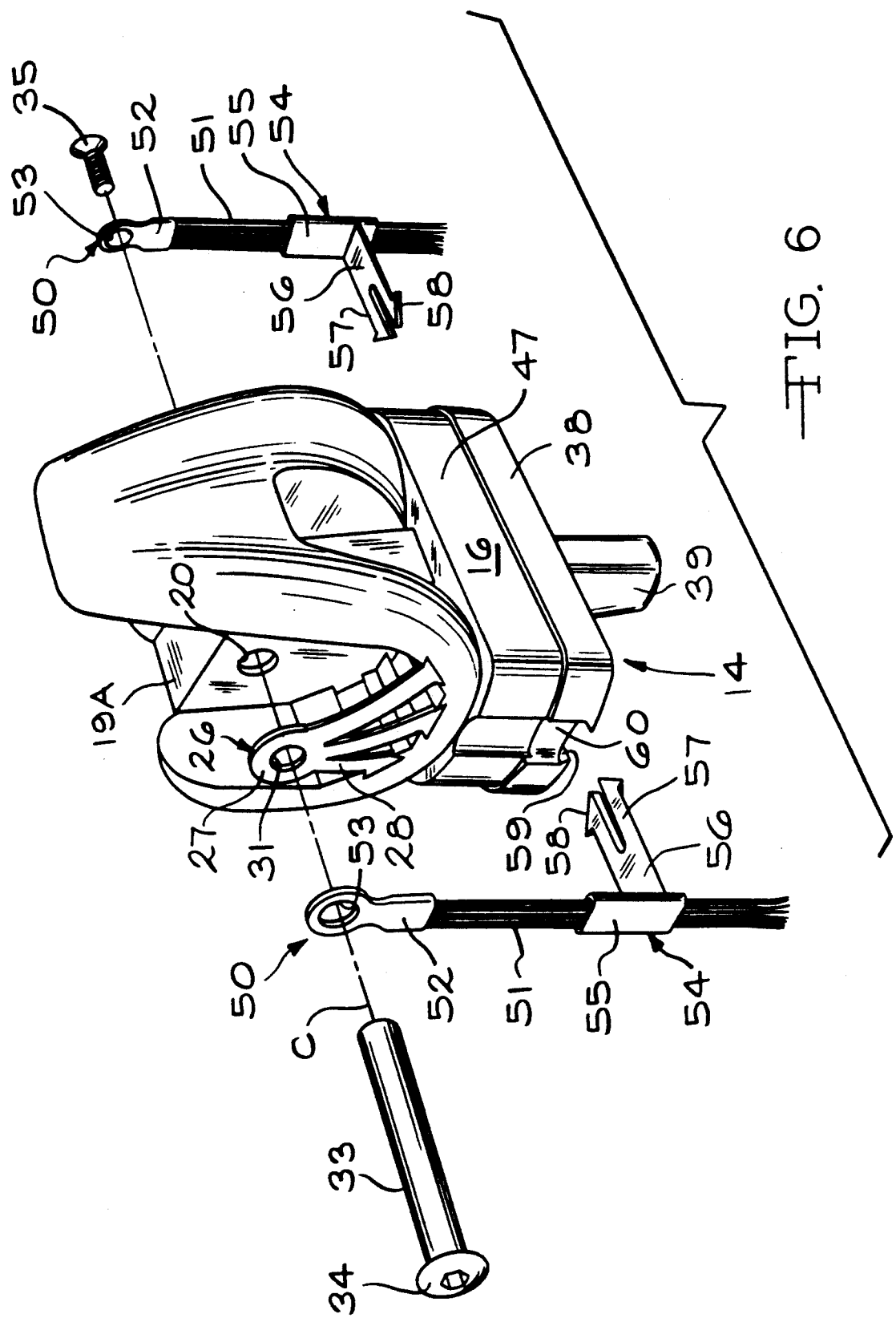
FIG. 6 is an exploded perspective view of one embodiment of the prosthesis of the present invention showing engagement of the femoral component, intermediate component and tibial component and with synthetic collateral ligaments positioned to be secured thereto.

A pair of hub members 26 are affixed to the femoral component 12, one at each lateral side of the condylar portions 18. The hub members 26 include a circular ring portion 27 from which extend a plurality of legs 28 each of which has a tine member 29 extending laterally inwardly and shaped to be snugly received in the dovetail slots 22. Each of the tines has an indentation 30 formed in its lower surface which receives the nub 23 for snugly retaining the tines 29 in the dovetail slots 22. The ring 27 has a central aperture 31 the center of which lies on the line C. The legs 28 may be planar as shown in FIG. 2 or may be bowed outwardly or laterally slightly as shown in FIGS. 5 and 6 to accommodate the anatomical structure of a patient having a large knee in order to minimize the amount of bone tissue required to be removed.

As is well known in the art, the femur and tibia are resectioned to receive the respective components of any knee prosthesis. See for example, the following documents which are incorporated herein by reference, copies of which are herewith enclosed: "Principles and Techniques of Knee Replacement" by John N. Insall, M.D., Albert H. Burstein, Ph.D., and M. A. R. Freeman, M.D., and a brochure entitled "Endo-Model TM Link Rotation Knee Joint Prosthesis", manufactured by Waldemar Link GmbH & Co., Hamburg, Germany and distributed by Link America, Inc., East Hanover, N.J. As can be seen from the foregoing documents; the condyles are resected to provide a series of planar surfaces which will be snugly engaged by the planar faces 21 A-E of the femoral component 12. With the femoral component 12 engaged to the prepared condyles and the hub members 26 engaged thereto with the tines 29 in the dovetail slots 22, a hole H may be drilled through each of the condyles in alignment with the line C defined by the apertures 31 of the hub members 26 and the apertures 20 formed in the housing 19.

A pin functioning as a pivot bar 33 is received in the apertures 20 and 31 and through the holes H drilled in the condyles. As can be seen in FIG. 2, 3 and 6, the pin/pivot bar 33 an enlarged head 34 at one end and is internally threaded at the other end to receive a flathead set screw 35 with deformed locking threads to insure against inadvertent loosening.

All portions of the femoral component 12 are formed of a suitable metal such as a cobalt chrome alloy, cobalt chrome molybdenum alloy, titanium alloy or stainless steel. For example, it may be a cobalt-chromium-molybdenum alloy produced according to the standards of the American Society for Testing Materials, ASTM F-75, manufactured and sold under the trademark Zimaloy ® which is a registered trademark of Zimmer, Inc., Warsaw, IN.

The tibial component 14 is also formed of a metal such as used for forming the femoral component 12. The tibial component 14 includes a tibial plateau 38 from which extends a stem 39 which is anchored in a prepared cavity of the tibia T with bone cement such as polymethylmethacryate as is well known in the art.

The intermediate tray or plateau 16, formed of a suitable plastic material such as ultra high molecular weight polyethylene, has encapsulated therein a metal reinforcing member 41 consisting of a flat base 42 and an integral upstanding wall 43 having an aperture 44 near its upper extent, centered on line C. The plastic portion of the intermediate tray or plateau 16 completely encapsulates the metal reinforcing member 41 and includes a pedestal 47 in which is formed a pair of laterally spaced apart oblong concavities 46 each of which receives one of the femoral component condylar portions 18 in sliding relationship therewith.

As can be seen particularly from viewing FIGS. 1 and 3, the outer surfaces of the condylar portions 18 which are formed of one of the previously mentioned metals engage and are supported in the concavities 46 of the plastic intermediate tray or plateau 16. As the knee is flexed, the highly polished condylar portions 18 move relative to the concavities 46 as the leg is moved between extension and flexion.

As is well-known, since the concavities are subjected to high compressive loads from the condylar portions 18 resting thereon in sliding relationship therewith as the knee is flexed, it is important that there be a low co-efficient of friction. This is achieved with the use of plastic material for the concavities 46.

A high column 48 extends superiorly from the portion of the pedestal 47 between the concavities 46. The column 48 is positioned in the space between the two condylar portions 18 and has a lateral extent less than the distance between the opposing side walls 19B of the housing 19 to provide a gap between the lateral surfaces of the column 48 and the inner surfaces of the respective opposing side walls 19B. The column 48 has a height such that, when positioned in the space between the condylar portions 18 as defined by the housing 19, it extends above the pivot bar 33 and line C but is spaced from the lower surface of the top wall 19A of the housing 19. The column 48 has an enlarged passageway 49 extending laterally therethrough through which the pin/pivot bar 33 extends to hingedly connect the intermediate tray or plateau 16 to the femoral component 12. As can be readily seen in FIG. 2, the passageway 49 is flared outwardly at each end to permit angular or toggling movement of the pin/pivot bar 33 relative to the wall of such passageway 49. This coupled with the gaps between the column 48 and the housing 19 permits some toggling movement between the column 48 and the housing and thereby permits the tibia to rotate inwardly as the knee is flexed downwardly from a position of extension to a position of flexion and approximates the rotation of the tibia in the normal function of an anatomical knee joint.

If desired and as shown in FIG. 2A, the pivot bar 33 may have a central portion 36 of reduced diameter to provide a larger space and thus permit additional angular rotation of the tibia during flexion.

Figure 12:
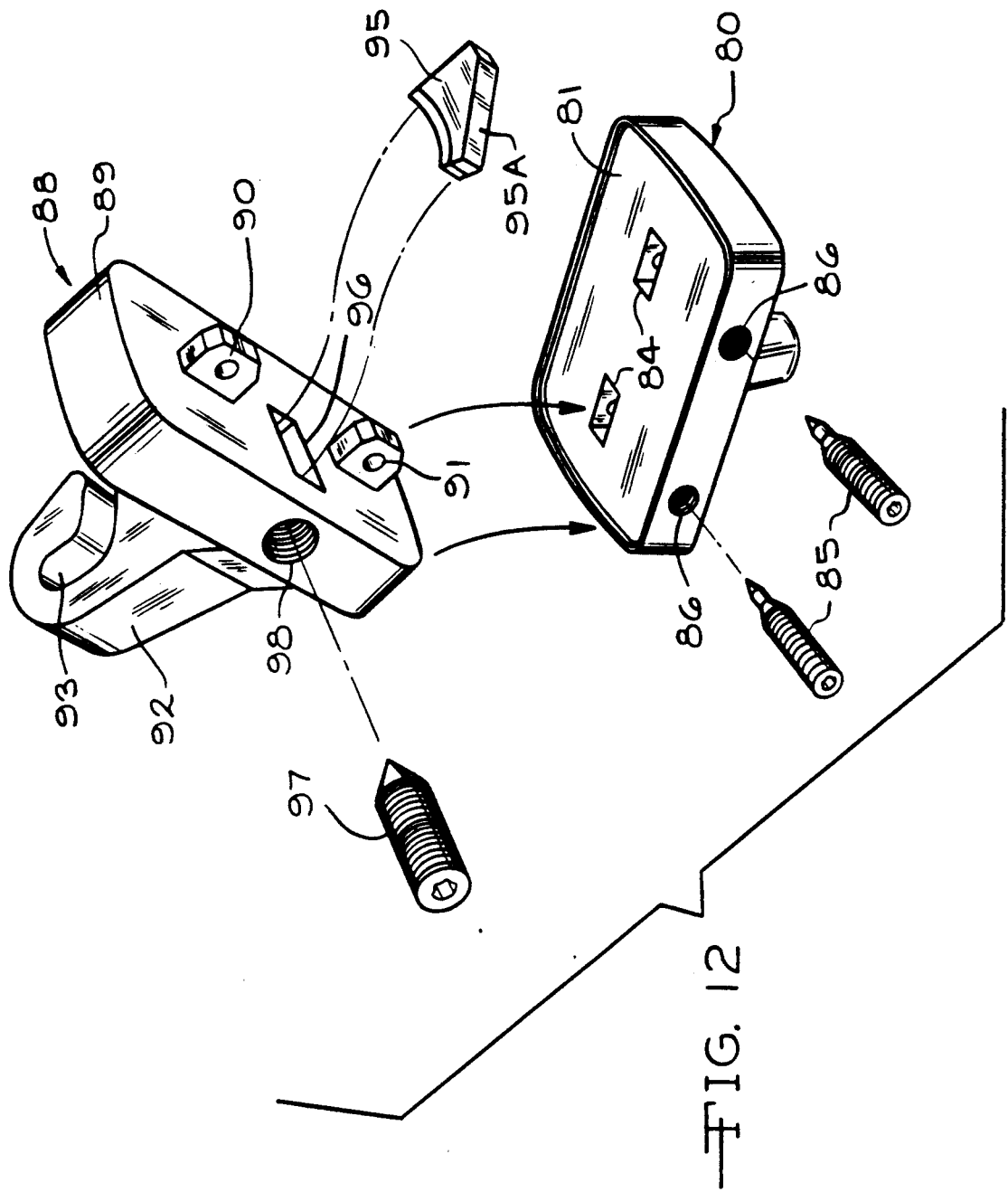
FIG. 12 is an exploded perspective of the tibial component and the intermediate component.

The intermediate tray or plateau 16 may be affixed to the tibial component 14 in any one of a number of ways including a snap or interference fit, pegs and fasteners including ones of the type to be described with reference to the embodiment of FIG. 12 or a tongue-and-groove arrangement of the type to be described with reference to the embodiment of FIGS. 15–20.

An added feature of the present invention provides additional support in the event of removal or severe deterioration of either or both of the two collateral ligaments, namely, the lateral and medial collateral ligaments. As may be seen clearly in FIGS. 1–6, a pair of synthetic collateral ligaments 50 may be joined between the femoral component 12 and the tibial component 14. The synthetic collateral ligaments 50 include a plurality of strands 51 of synthetic, non-reactive, non-absorbable biocompatible material such as Gore-Tex ® manufactured by W. L. Gore & Associates, Flagstaff, Ariz., which are crimped in an eyelet 52 having an aperture 53 sized to receive the pivot bar 33 if positioned, on the medial side or the set screw 35 if positioned on the lateral side. If desired, the strands could be biodegradable rather than non-absorbable or a combination of both of biodegradable and non-absorbable. For example, biodegradable material such as those used for sutures may be used for the strands 51. Such biodegradable sutures are well known in the art and include ones made of polylactic or polyglyconic material such as those sold under the trademark Vicryl ® by Ethicon, those sold under the trademark DEXON ® by Davis-Geck and those sold under the trademark P.D.S. ® by Ethicon.

As will be appreciated and as is well known in the art, the femoral component 12 may be manufactured in a number of sizes having different radii R for the apex of the condylar portions 18 and will have varying thicknesses for the pedestal 47 of the intermediate tray or plateau 16. Accordingly, it is not possible to predict in advance the precise length of synthetic strands 51 to be used for the synthetic collateral ligaments 50. This uncertainty may be overcome by providing a pair of fasteners 54 for joining the synthetic strands 51 to the opposing collateral sides of the tibial component 14 of the type which permit movement of such fasteners 54 relative to the strands 51 during the step of affixing the synthetic collateral ligament 50 to the tibial component 14. The fasteners 54 are formed of a metal such as titanium, or other compatible material which is suitable for implantation in the human body and which is also suitable for crimping of the body 55 to firmly engage the synthetic strands 51.

As shown particularly in FIG. 6, the fastener 54 includes a body portion 55. Extending laterally inwardly from the body 55 at substantially right angles thereto is an arm member 56 from which extends a pair of dovetail locking tabs 57, each having an enlarged head 58.

The surgeon will determine the appropriate length for the strands 51 and will then crimp the properly adjusted body portion 55 therearound. Following such crimping, the portion of the strands 51 extending beyond the body 55 may be trimmed. The tibial component 14 has a pair of dovetail slots 59, one extending to each lateral extremity for receiving the arms 56 and dovetail locking tabs 57 with the enlarged heads 58 therein. A notch 60 is formed in each collateral edge of the tibial component 14 and intermediate tray or plateau 16 to receive the body 55 and synthetic strands 51 of the respective synthetic collateral ligaments 50.

Referring to FIG. 3A, there is shown an alternate form of synthetic collateral ligaments 50' having a modified fastener 54'. In this embodiment, the fastener 54' has a body 55' with a flared out open area at the top and two spaced apart passageways 68A and 68B which are separated by a wall 69 extending between the interior wall of the body 55' from which the arm 56' extends and the opposite or exterior wall. Under this embodiment, the strands 51 are separated into two groups 51A and 51B and the group 51A is passed through the passageway 68A and the group 51B is passed through the passageway 68B. As can be seen from FIG. 3A, a sufficient length of each group 51A and 51B extends beyond the end of the respective passageways 68A and 68B to permit a surgical knot to be tied following adjustment of the fastener 54' to the proper position in the tibial component 14 and relative to the groups 51A and 51B of strands 51. Preferably, the wall 69 does not extend to the bottom of the body 55' thus leaving a recess 63 in which the knot can be buried or received.

As can be clearly seen from viewing FIGS. 1 and 3, showing movement of the knee from extension to flexion, the distance from the centerline C to the intermediate tray or plateau 16 remains constant throughout such movement as a result of the fact that the condylar portions 18 follow a uniform radius along the antero-posterior extent. Accordingly, the amount of tension on the synthetic strands 51 remains substantially but not completely uniform throughout movement from extension to flexion. The slight variation in tension will result from the rotational movement of the tibial component 14 and tibial tray or plateau 16 relative to the femoral component 12 during flexion which is permitted as a result of the passageway 49 being enlarged from the size of the pivot bar 33 and the spaces between the column 48 and the housing 19 thus permitting some rotational and toggling movement between such pivot bar 33 and the column 48.

The prosthesis embodiment of FIGS. 1–6 also provide stop means intended to prevent excessive flexion, i.e., flexion beyond about 120° from full extension. The pedestal 47 of the intermediate tray or plateau 16 has formed in the superior face in alignment with the column 48 and on the anterior side a tapered recess 62 which will be engaged by the leading edge of the top wall 19A of the housing 19 when the knee is in maximum flexion as shown in FIG. 3.

Referring now to FIGS. 7-12, for some applications it is desirable that the spaced apart condylar portions of the femoral component follow a contour which is curved along the antero-posterior extent other than along a uniform radius. The purpose of this is to provide a somewhat flatter and, thus, greater contact area between the condylar portions and the concavities of the intermediate tray or plateau when the leg is in extension and the prosthesis subjected to maximum compressive loads from the weight of the person while standing and a sharper curve when in flexion and subjected to smaller compressive loads. A description of the desirability of having large bearing areas may be found in U.S. Pat. Nos. 3,996,624, 4,301,553 and 5,011,496 which are incorporated herein by reference.

The embodiment of FIGS. 7-12 permit the use of a hinge on a prosthesis in which the condylar portions follow along the antero-posterior extent, a path other than circular and, thus, permitting the utilization of a larger surface area for absorbing compressive forces than is possible with condylar portions following a circular path.

Referring to FIGS. 7-12, there is provided a femoral component 70 having a fixation shank 71 intended for implantation in a prepared intramedullary canal of the femur F. Depending upon the condition of the femur, it may be desirable to utilize a shank extension 72 to provide additional support; however, the prosthesis of the present invention may be used with or without such shank extension 72. Femoral and tibial stem extensions are well known in the art and do not in and of themselves form the invention claimed herein.

Figure 7:
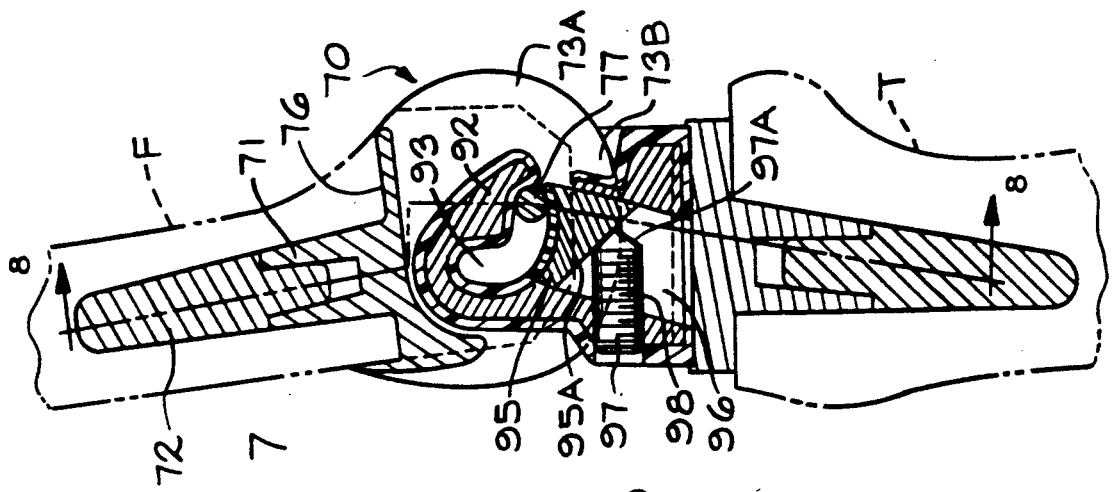
FIG. 7 is an elevational view, in section, showing a modified embodiment.
Figure 9:
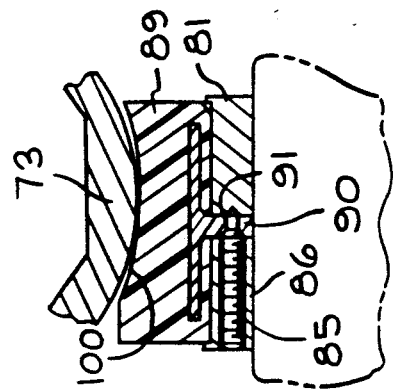
FIG. 9 is a sectional view taken through line 9—9 of FIG. 8.

The femoral component 70 includes a pair of identical spaced apart condylar portions 73, each of which has an outer surface smoothly convexly curved in lateral profile and convexly curved along the antero-posterior extent but, in contrast to the embodiment of FIGS. 1-6, following not a circular path, but rather a curved path which is flatter and has a larger radius in some areas than in others. Thus, as can be seen in FIGS. 7, 10 and 11, the area of the condylar portion 73 designated 73A follows a much sharper curve having a shorter radius than the area designated 73B. Accordingly, there is a greater bearing surface area between the area designated 73B and the adjacent concavities of the intermediate tray than between the area designated 73A and the concavities. As shown in FIG. 7, the femoral component 70 is designed so that the condylar portion 73 area designated 73B is engaged to the concavities when the leg is in extension (FIG. 7) and the prosthesis potentially subjected to maximum compressive loads. When it is in flexion (FIGS. 10 and 11) and thus is subjected to lower compressive loads, the area 73A having a sharper curvature/shorter radius and therefore smaller bearing surface area is in contact with the concavities. The present embodiment permits the utilization of a femoral component having such non-circular shape condylar portions while still permitting the utilization of the hinged concept.

The femoral component 70 includes a housing-like structure which interconnects the condylar portions 73 and includes a pair of laterally spaced apart side walls 74 joined by a top wall 76 from which extends the fixation shank 71. A pivot bar 77 extends between the side walls 74.

A tibial component 80 includes a tray 81 and a fixation post 82 positioned in the prepared intramedullary canal of the tibia T. If the condition of the patient warrants, a post extension 83 may also utilized.

An intermediate tray or plateau 88 is affixed to the tray 81 of the tibial component 80. As in the embodiment of FIGS. 1-6, the femoral component 70 and tibial component 80 are formed of suitable metal required to provide structural strength to the prosthesis over long periods of implantation and the intermediate tray or plateau 88 is suitable metal encapsulated or substantially encapsulated in a suitable surgical grade low friction plastic such as ultra high molecular weight polyethylene. The intermediate tray or plateau 88 includes a pedestal 89 having a lower surface mounted on the tray 81 of the tibial component 80. A pair of metallic lock tabs 90, each having an aperture 91, extend downwardly from the pedestal 89. The tray 81 of the tibial component has a pair of recesses 84 sized and positioned to receive the lock tabs 90. Threaded passageways 86 extend from an edge of the tray to each of said recesses 84. A pair of set screws 85 are engaged in the threaded passageways 86 and have a conical dog point or similar extension to engage the apertures 91 in the pedestal lock tabs 90. (See FIG. 9).

Extending upwardly from the pedestal 89 of the intermediate tray or plateau 88 is a hook member 92 defining an arcuate contoured slot 93 intended to engage the pivot bar 77 of the femoral component 70. Means are provided to retain the pivot bar 77 in the slot 93 following engagement of the hook member 92 to the pivot bar 77 during the surgical procedure. Such retention means includes a contoured and tapered locking member 95 positioned in a tapered recess 96 of the pedestal 89. The recess 96 and the locking member 95 employ matching tapers so designed that upon insertion of the locking member 95 in the recess 96 to the maximum extent permitted by the respective tapers, the locking member 95 will have its upper face meeting smoothly with that portion of the hook member 92 forming the slot 93 so that the upper surface of such locking member 95 will cooperate with the opposing portion of the hook member 92 to form an extension of such slot and, thus, permit relative movement between the pivot bar 77 and the hook member 92 within the open end portion of the slot 93. As will be noted particularly in FIG. 7, the contour of the hook member 92 and the locking member 95 at the open end of the slot 93 is such as to produce a narrowed gap, one which is smaller than the diameter of the hook member 92. This insures that the hook member 92 does not inadvertently pull out of the slot 92 and become disengaged with the pivot bar 77.

The locking member 95 is retained in the recess 96 by means of a socket head set screw 97 screwed into a threaded passageway 98 in the pedestal 89 with its leading end engaged to the tapered lower face 95A of the locking member 95. The set screw 97 leading end has a tapered conical face 97A which, preferably, is tapered at the same angle as the lower face 95A of the locking member. This will cause the locking member 95 to be urged firmly and snugly against the tapered walls into its fully seated position as shown in FIG. 7.

As in the previous embodiment, the pedestal 89 of the intermediate tray or plateau 88 has a pair of concavities 100 upon which the condylar portions 73 will rest and move thereagainst as the knee is moved from extension to flexion.

FIGS. 10 and 11 show movement and the relative positioning of the pivot bar 77 in the slot 93 as the knee is moved from extension position of FIG. 7 to flexion in FIGS. 10 and 11. As can be seen in FIGS. 7, 10 and 11, the contour of the slot 93 in relation to the contour of the concavities 100 along their antero-posterior extent is such that movement of the knee from extension to flexion will cause the pivot bar 77 to move further into the slot 93 so that the condylar portions 73 can move with relatively uniform pressure and uniform tracking as the knee is flexed. Thus, the contour of the slot 93 is so designed in relation to the contour of the condylar portions 73 along their antero-posterior extent to insure that the condylar portions 73 are in contact with the concavities 100 as the knee is moved between positions of extension and flexion and that movement of the hook member 92 relative to the pivot bar 77 does not pull the condylar portions 73 out of engagement with the concavities 100 or cause them to bind in such concavities.

Figure 8:
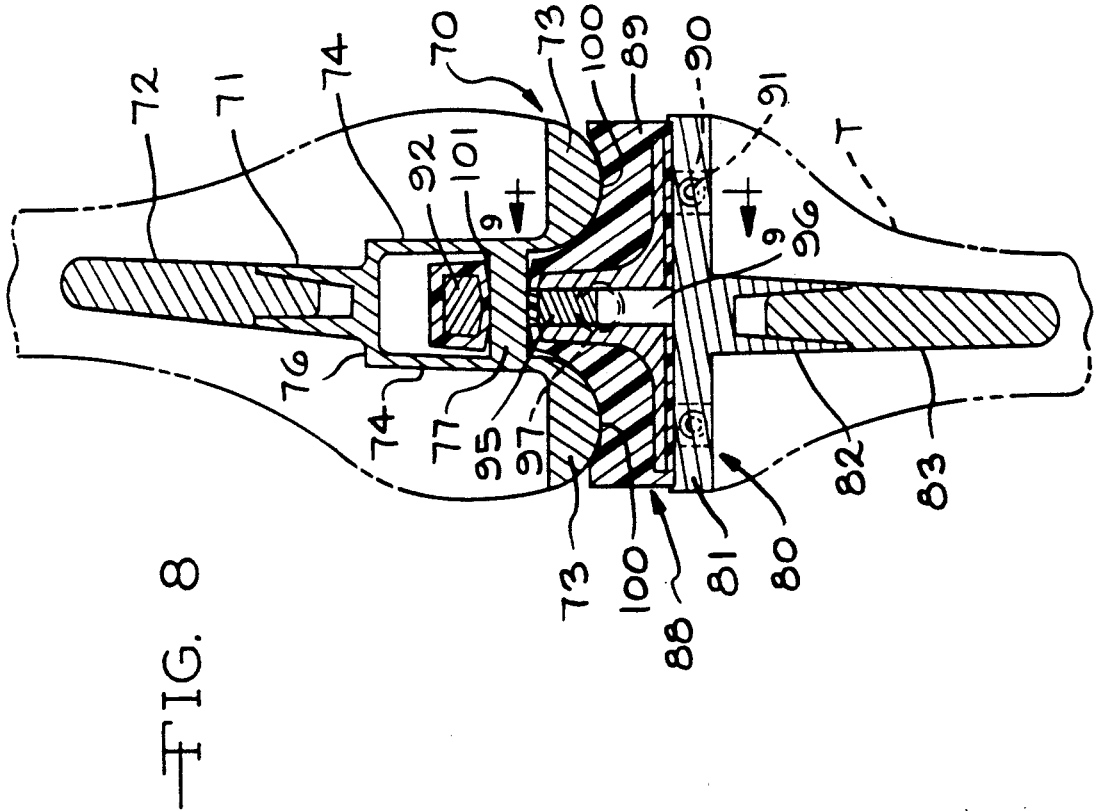
FIG. 8 is a sectional view taken through line 8—8 of FIG. 7.

As can be seen, particularly in FIG. 8, gaps 101 are provided at the lateral extremities of the slot 93 to permit toggling and thus accommodate axial rotation of the tibia as the knee is moved from extension to flexion to thereby approximate motion of the natural knee.

FIGS. 13 and 14 show another embodiment utilizing a hook in combination with a pivot bar. In this embodiment, there is provided a femoral component 70' in which there is provided condylar portions 73' which follow a uniform circular arc along their antero-posterior extent. As in the embodiment of FIGS. 7-12, there is provided a housing having side walls 74', a top wall 76' and a pivot bar 77' extending between the side walls 74'. In this embodiment, the center of the pivot bar lies on the center of radius for the circular arc followed by the condylar portions 73' along their antero-posterior extent.

No fixation post is shown in the femoral component 70' of this embodiment; however, if the condition of the patient required, one could be provided.

There is also provided a tibial component 80' which is similar to the tibial component 80 of the embodiment of FIGS. 7-12 with the exception that it has a fixation post 82' that has no provision for an extension.

Under this embodiment the intermediate tray or plateau 88' has a hook member 92' with a slot 93' which defines an arc of a circle. A lock member 95' is retained in recess 96' by set screw 97' threadedly engaged in the passageway 98' to wedge the lock member 95' snugly in the tapered recess 96' so that its upper end substantially closes the slot 93' to prevent inadvertent disengagement of the hook member 92' from the pivot bar 77'.

If desired, synthetic ligaments may be used in the embodiments of FIGS. 8-14.

Referring now to FIGS. 15-20, there is shown yet another embodiment utilizing synthetic ligaments but with no hinge securing the respective components together. Under this embodiment, there is provided a femoral component 112, a tibial component 114 and an intermediate tray or plateau 116.

The femoral component 112 includes a pair of spaced apart condylar portions 118 which are convexly curved along the antero-posterior extent and following a non-circular path such as that described with reference to the embodiment of FIGS. 7-12. Integral with and positioned between the condylar portions 118 is a central housing 119 having a top wall 119A and side walls 119B extending between the top wall 119A and the condylar portions 118. A pair of threaded passageways 120 extend into the top wall 119A, one from the upper portion of each of the side walls 119B. A fixation shank 124 extends superiorly from the top wall 119A. As in the previous embodiments, the interior of the condylar portions 118 include a plurality of planar faces 121A, 121B, 121C, 121D and 121E. As in the embodiment of FIGS. 1-6, three of the planar surfaces, namely, 121B, 121C and 121D have dovetail slots 122 each of which has a raised nub 123.

A pair of hub member 126 are affixed to the femoral component 112, one at each collateral side of the condylar portions 118. The hub member 126 include a circular ring portion 127 from which extend a plurality of legs 128 each of which have a tine member 129 extending laterally inwardly and shaped to be snugly received in the dovetail slots 122. Each of the tine members 129 has a recessed circular shaped indentation 130 formed in its lower surface which is engaged by one of the nubs 123 for snugly retaining the tines 129 in the dovetail slots 122. The ring portion 127 has a central aperture 131 each of which is aligned with one of the threaded passageways 120. A stud 125 extends through the circular ring portion 127 and is threadedly engaged in each passageway 120. Each of the studs 125 has an annular groove 133 positioned at the end portion of the stud extending laterally beyond the hub member 126.

The tibial component 114 includes a tibial plateau 138 from which extends a fixation shank 139 which is anchored in a prepared cavity of the tibia T. In this embodiment, the tibial plateau 138 has formed therein a dovetail recess 132 for receiving and retaining the intermediate tray or plateau 116.

The intermediate tray or plateau 116 is similar to that of the embodiment of FIGS. 1-6 and includes a metal reinforcing member 141 consisting of a flat base 142 and an upstanding wall 143. A suitable plastic material encapsulates the metal reinforcing member 141 except for the surface of the flat base 142 adjacent the tibial plateau 138 and the upper end of the upstanding wall 143. The plastic material is contoured to form a pair of laterally spaced apart oblong concavities 146 each of which receives one of the femoral condylar portions 118. A column 148 extends superiorly from the portion of the intermediate tray or plateau 116 between the concavities 146. As can be seen particularly in FIG. 16, the column 148 in this embodiment has a height such that it is spaced from the lower or interior surface of the top wall 119A of the housing 119. The column 148 is positioned in the space between the two condylar portions 118 as defined by the interior surfaces of the opposing side walls 119B of the housing and has a lateral extent such that it is spaced from such interior surfaces.

Figure 18:
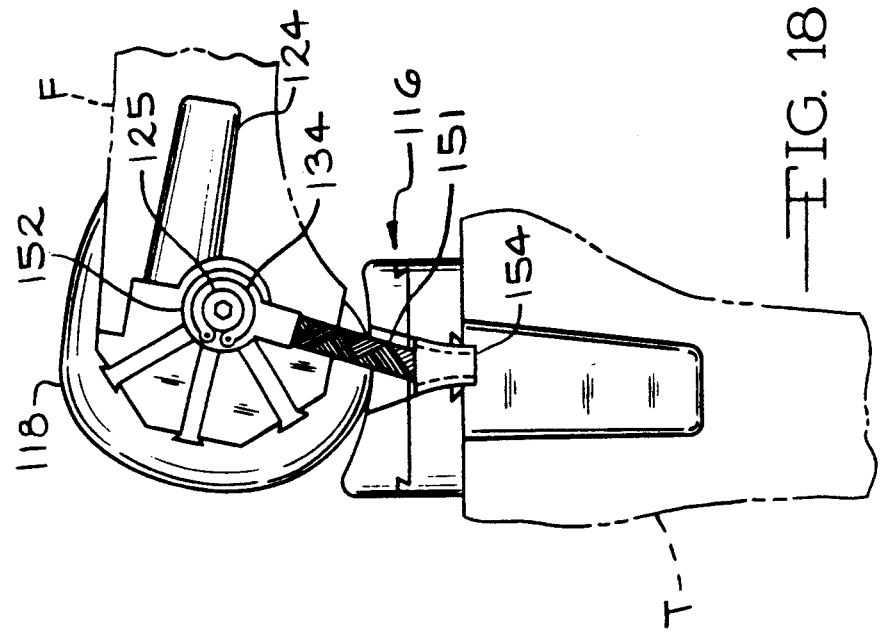
FIG. 18 is a view similar to FIG. 15 showing the relative position of the components with the knee in flexion.
Figure 17:
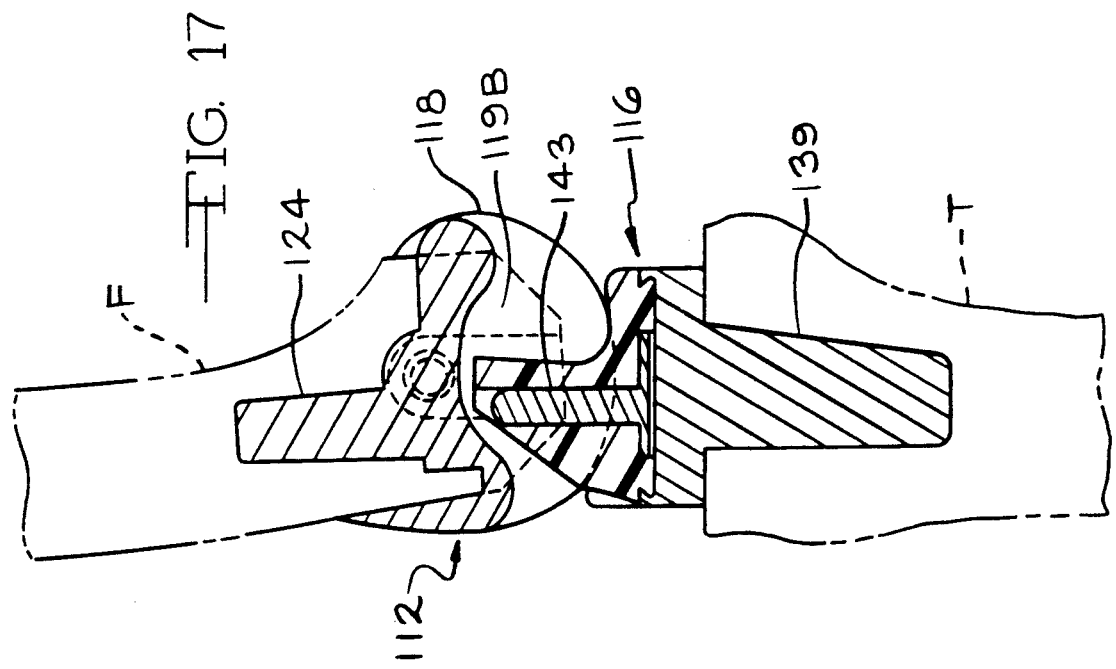
FIG. 17 is a sectional view of the embodiment shown in FIG. 15 showing the relative position of the components with the knee in extension.
Figure 20:
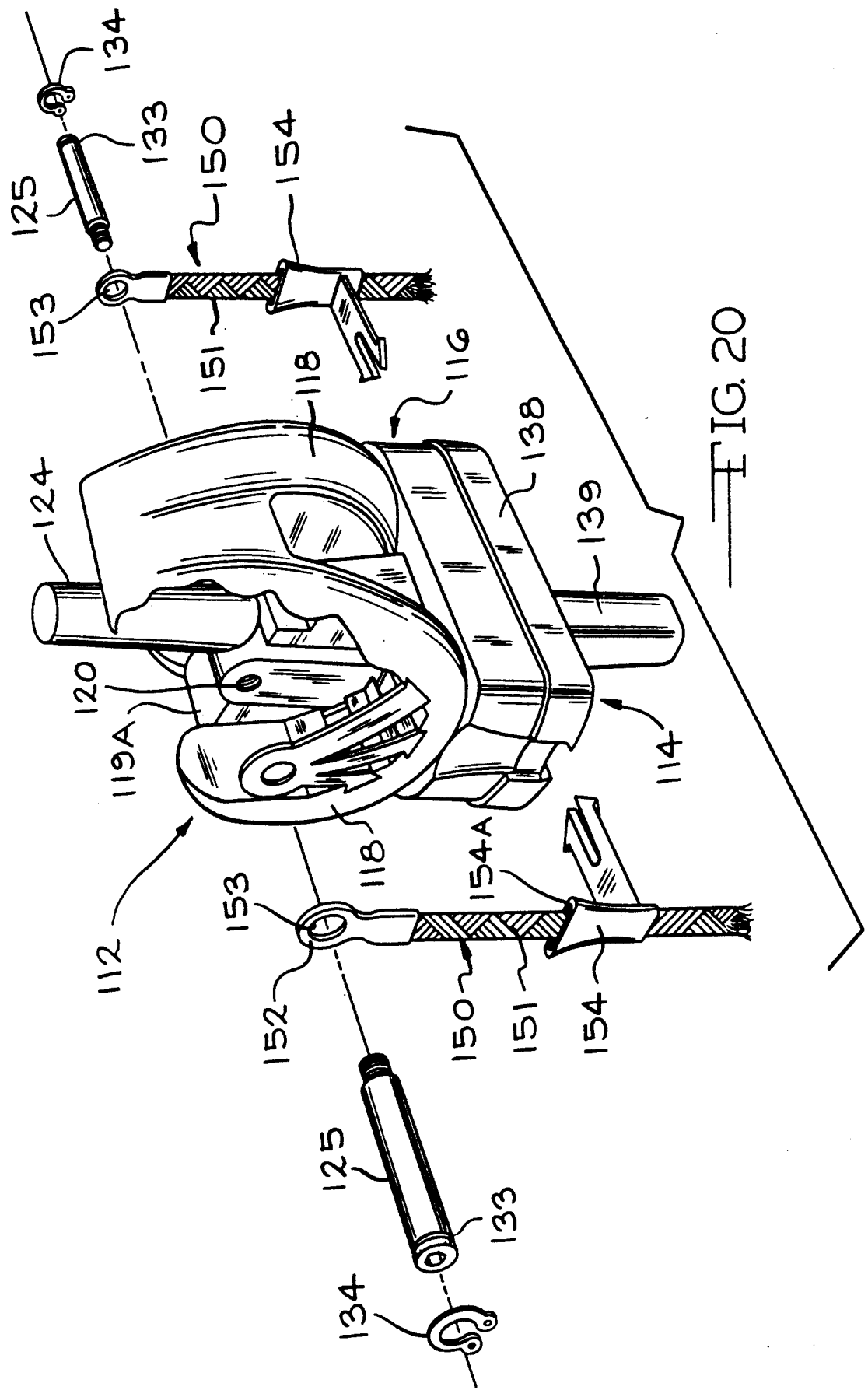
FIG. 20 is a partially exploded perspective view showing the complete prosthesis of the embodiment of FIGS. 15-18.

A pair of synthetic collateral ligaments 150 may be joined between the femoral component 112 and the tibial component 114. As previously noted, the condylar portions 118 of the femoral component of this embodiment follow a non-circular path in order to provide a greater bearing surface area between such condylar portions 118 and the concavities 146 of the intermediate tray or plateau 116 when the knee is extended. As a result, as the knee flexes from the position of extension shown in FIG. 15 to flexion as shown in FIG. 18, the distance from the center of the studs 125 to the tibial component 114 will vary. Accordingly, the synthetic collateral ligaments 150 are provided in stretchable form such as by interweaving the strands 151 as shown in FIGS. 15, 16 and 18, or by other means providing a stretchable synthetic ligament.

As in the embodiment of FIG. 1, the synthetic collateral ligaments 150 at one end may be crimped in an eyelet 152 having an aperture 153 sized to be telescoped over the end of the respective studs 125. A retaining clip 134 is snapped in the annular groove 133 at the end of the stud 125 to secure the eyelet 152 of each of the synthetic collateral ligaments 150 to each of the studs 125.

The opposite ends of the synthetic collateral ligaments 150 are retained in a fastener 154 which is joined to the tibial component 114 in any desired manner including that described in connection with the embodiment of FIGS. 1–6. The fastener 154 is flared outwardly as its upper portion 154A in order to accommodate movement of the synthetic collateral ligament 150 from a near vertical position when the knee is in extension (FIG. 15) to a slightly angled position when it is in flexion (FIG. 18) in order to insure that the weaved strands 151 do not rub against the metal fastener 154.

The total knee prosthesis of the present invention is one which is particularly well suited for total knee replacement including ones in which the medial and lateral collateral ligaments are damaged or otherwise deficient. Under various embodiments, a hinge fixture may be used irrespective of whether the condylar portion has a circular or non-circular configuration along its antero-posterior extent. If the medical condition of the patient warrants the use of synthetic collateral ligaments, it is possible and within the contemplation of the present invention to use ones which are biodegradable and, thus, absorbable within the body over time. In such event, scar tissue may replace such absorbable ligaments and will then function to provide the collateral support. The synthetic ligaments could also be a combination of some strands being biodegradable absorbable and others being non-absorbable.

Many modifications will become readily apparent to those skilled in the art. Accordingly, the scope of the present invention should be determined solely by the scope of the appended claims.

I claim:

1. A prosthetic knee joint comprising:
   (a) a femoral component having a condylar portion defining a pair of spaced apart convex bearing surfaces, a housing having side walls between said bearing surfaces and pivot bar means extending from said side walls, said femoral component having a lateral collateral side and a medial collateral side;
   (b) a tibial component including fixation means for affixing to a tibia, said tibial component having a pair of spaced apart concavities engaged by said convex bearing surfaces and a column between said concavities extending toward said femoral component between said side walls; and
   (c) support means connected to said pivot bar means for connecting said femoral component to said tibial component, said support means permitting relative movement between said femoral component and said tibial component; said support means comprising synthetic prosthetic ligament means on at least one of said collateral sides having a first end and a second end and having means for joining said first end to said pivot bar and said second end to said tibial component.

2. A prosthetic knee joint according to claim 1, wherein said ligament means includes a plurality of strands and further including adjustment means for adjusting the length of said strands.

3. A prosthetic knee joint according to claim 2, wherein said adjustment means includes a fastener having a body encircling said strands, said body being moveable relative to said strands and means for fixing said body relative to said strands.

4. A prosthetic knee joint according to claim 31, wherein said means for fixing said body relative to said strands comprises crimped walls tightly engaging said strands.

5. A prosthetic knee joint according to claim 31, wherein said means for fixing said body relative to said strands includes at least two passages in said body and wall means separating said passages, a first portion of said strands positioned in one passage and a second portion of said strands positioned in the other of said passages and means for joining together said first and second portions.

6. A prosthetic knee joint according to claim 1, further including means for securing said ligament means to said femoral and tibial components, said securing means including means for adjusting the length of said prosthetic ligament means.

7. A prosthetic knee joint according to claim 1, wherein said ligament means is stretchable.

8. A prosthetic knee joint according to claim 7, wherein said ligament means includes a plurality of synthetic strands which are stretchable.

9. A prosthetic knee joint according to claim 7, wherein said ligament means includes a plurality of synthetic strands interwoven to form a stretchable length.

10. A prosthetic knee joint according to claim 1, further including a hub member comprising a ring defining an aperture encircling said pivot bar, a plurality of legs extending from said ring along said collateral side and tine members extending laterally from said legs and joined to said condylar portion.

11. A prosthetic knee joint according to claim 19, wherein said support means comprises said column and a passageway extending transversely through said column from a first end to a second end and said pivot bar means extends through said passageway.

12. A prosthetic knee joint according to claim 11, wherein said passageway has a substantially circular cross-sectional configuration larger in size than said pivot bar means.

13. A prosthetic knee joint according to claim 12, wherein said passageway has a larger size at said first and second ends than at other portions.

14. A prosthetic knee joint according to claim 11, wherein said pivot bar means has a reduced cross-sectional size in the area aligned with said passageway.

15. A prosthetic knee joint according to claim 11, wherein said support means comprises said column, said column being in the shape of a hook defining said passageway, said pivot bar means extending through said passageway.

16. A prosthetic knee joint according to claim 19, wherein said support means comprises said column, said column being in the shape of a hook defining a passageway, said pivot bar means extending through said passageway, said passageway following a non-circular curved path in a direction transverse to said pivot bar means.

17. A prosthetic knee joint according to claim 19, wherein said tibial component includes a tibial plateau and said support means comprises said column extending from said tibial plateau and defining a hook having a passageway through which said pivot bar extends, said hook having a peripheral opening defining a peripheral entrance to said passageway for said pivot bar means, and means for at least partially closing said peripheral opening to prevent removal of said pivot bar through said peripheral entrance.

18. A prosthetic knee joint according to claim 17, wherein said passageway follows a non-circular curved path in a direction transverse to said pivot bar means.

19. A prosthetic knee joint comprising
(a) a femoral component having a condylar portion defining a pair of spaced apart convex bearing surfaces, a housing having a pair of spaced apart side walls extending upwardly from said bearing surfaces and pivot bar means extending from each of said side walls, said femoral component having a lateral collateral side and a medial collateral side;
(b) a tibial component including fixation means for affixing to a tibia, said tibial component having a pair of spaced apart concavities engaged by said convex bearing surfaces and a column between said concavities extending toward said femoral component between said side walls; and
(c) support means connected to said pivot bar means for connecting said femoral component to said tibial component, said support means permitting relative movement between said femoral component and said tibial component.

20. A prosthetic knee joint comprising
(a) a femoral component having fixation means for affixing to a femur and a pair of spaced apart first and second condylar portions with convex bearing surfaces, said femoral component having a lateral collateral side and a medial collateral side, said first condylar portion adjoining one of said collateral sides and said second condylar portion adjoining the other of said collateral sides;
(b) a tibial component including fixation means for fixing to a tibia, said tibial component having a lateral collateral side and a medial collateral side;
(c) flexible synthetic prosthetic ligament means having a first end secured to at least one of the collateral sides of said femoral component and a second end secured to at least one of the collateral sides of said tibial component, said prosthetic ligament means permitting relative rotation between said femoral and tibial components;
(d) means for securing said flexible synthetic prosthetic ligament means to said femoral component and to said tibial component, said means for securing comprising a hub member which includes a ring defining an aperture, a plurality of legs extending from said ring along said collateral side of said first condylar portion and tine members extending laterally from said legs inwardly toward said second condylar portion and joined to said first condylar portion, post means engaged to said hub member and means for fastening said flexible synthetic prosthetic ligament means to said post means.

21. A prosthetic knee joint according to claim 20, further including a housing between said condylar portions, said housing including spaced apart side walls and aperture means in said side walls, said aperture means of at least one of said side walls being aligned with said aperture of said ring, said post means extending into said aperture means of at least one of said side walls and said aperture of said ring.

22. A prosthetic knee joint according to claim 21, wherein each of said convex bearing surfaces follow a circular path along the anteroposterior extent of said femoral component, each said circular path having a predetermined radius measured from a center and said side wall aperture means lie on a line extending through each of said centers.

23. A prosthetic knee joint according to claim 21, wherein said tibial component includes a base member including said fixation means and a plateau member, said plateau member having a pair of spaced apart concavities, each of which receives one of said convex bearing surfaces and a column between said concavities extending into the space defined by said housing side walls, said column having a passageway receiving said post means.

24. A prosthetic knee joint according to claim 23, wherein said post means has a predetermined cross-sectional size and said column passageway defines an opening larger than said predetermined cross-sectional size.

25. A prosthetic knee joint according to claim 24, wherein said post means has a cross-sectional size in the area positioned in said passageway smaller than said predetermined cross-sectional size.

26. A prosthetic knee joint comprising
(a) a femoral component having fixation means for affixing to a femur and a pair of spaced apart first and second condylar portions with convex bearing surfaces, said femoral component having a lateral collateral side and a medial collateral side, said first condylar portion adjoining one of said collateral sides and said second condylar portion adjoining the other of said collateral sides;
(b) a tibial component including fixation means for fixing to a tibia, said tibial component having a lateral collateral side and a medial collateral side;
(c) flexible synthetic prosthetic ligament means with a plurality of strands having a first end secured to at least one of the collateral sides of said femoral component and a second end secured to at least one of the collateral sides of said tibial component, said prosthetic ligament means permitting relative rotation between said femoral and tibial components; and
(d) means for adjusting the length of said strands, said means including a fastener having a body encircling said strands, said body being moveable relative to said strands and means for fixing said body relative to said strands.

27. A prosthetic knee joint according to claim 26, wherein said means for fixing said body relative to said strands comprises crimped walls tightly engaging said strands.

28. A prosthetic knee joint according to claim 26, wherein said means for fixing said body relative to said strands includes at least two passages in said body and wall means separating said passages, a first portion of said strands positioned in one passage and a second portion of said strands positioned in the other of said passages and means for joining together said first and second portions.

* * * * *